United States Patent [19]

Ryan et al.

[11] Patent Number: 4,757,816
[45] Date of Patent: Jul. 19, 1988

[54] TELEMETRY SYSTEM FOR IMPLANTABLE PACER

[75] Inventors: Terence Ryan, Freemont, Calif.; Richard C. Regna, Miami, Fla.

[73] Assignee: Telectronics, N.V., Netherlands Antilles

[21] Appl. No.: 8,745

[22] Filed: Jan. 30, 1987

[51] Int. Cl.[4] ............................................. A61N 1/16
[52] U.S. Cl. ............................ 128/419 PT; 128/697; 128/903
[58] Field of Search ................... 128/419 PG, 697 PT, 128/903, 904

[56] References Cited

U.S. PATENT DOCUMENTS

| | | | |
|---|---|---|---|
| 3,212,496 | 10/1965 | Preston | 128/903 |
| 3,646,606 | 2/1972 | Buxton et al. | 128/696 |
| 3,713,449 | 1/1973 | Mulier | 128/419 PG |
| 3,746,005 | 7/1973 | Thaler et al. | 128/419 PG |
| 3,746,006 | 7/1973 | Thaler | 128/419 PG |
| 3,921,621 | 11/1975 | Bagssler | 128/903 |
| 3,960,140 | 6/1976 | Buxton | 128/696 |
| 4,159,018 | 6/1979 | Brastad | 128/697 |
| 4,441,498 | 4/1984 | Nordling | 128/419 P |
| 4,556,063 | 12/1985 | Thompson et al. | 128/903 |
| 4,562,840 | 1/1986 | Batina et al. | 128/419 PT |
| 4,585,004 | 4/1986 | Brownlee | 128/903 |
| 4,586,508 | 5/1986 | Batina et al. | 128/419 PG |

Primary Examiner—William E. Kamm
Attorney, Agent, or Firm—George H. Gerstman

[57] ABSTRACT

A telemetry system for transmitting digital data from an implanted pacer to an external programming/receiver unit includes a voltage-controlled pulse generator having an output period proportional to its input voltage magnitude. The external receiver unit includes a pulse period detector to generate a reconstructed analog signal whose amplitude is proportional to each pulse-to-pulse time interval from the pulse generator. The pulse generator requires only minimum width pulses and thus there is minimum system drain because the signal information is contained only in the pulse-to-pulse interval and not in the pulsewidth.

12 Claims, 2 Drawing Sheets

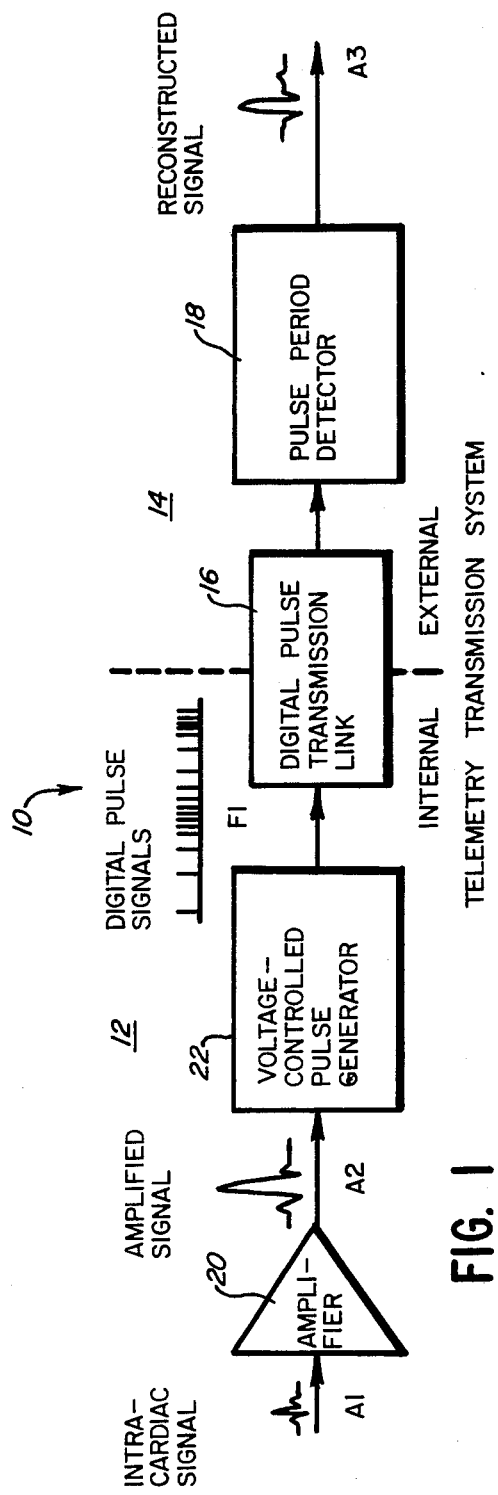
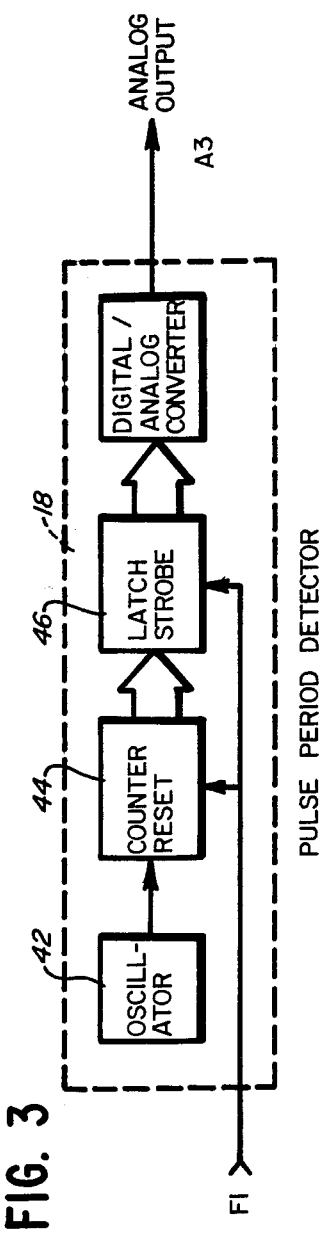

TELEMETRY SYSTEM FOR IMPLANTABLE PACER

BACKGROUND OF THE INVENTION

This invention relates generally to telemetry systems for physiological implants and more particularly, it relates to a telemetry system for transmitting internal signals from an implanted cardiac pacer to an external programming/receiver unit which utilizes a pulse generator having an output period proportional to its input voltage magnitude.

In the field of implanted cardiac pacers, there has been developed in the prior art a variety of telemetry systems for signalling out data from the implanted pacer. However, many of these prior art systems relied on the use of telemetered data which was based upon analog information transmission. As a result, these prior art telemetry systems encountered the problem of distortion in the recovery of the telemetered analog data from the pacer as the distance between the pacer and the external receiver unit changed. Another problem associated with implanted pacers is the lacking of information relating to conditions of the pacer such as the remaining life of the battery, the pulse voltage and the pulse current.

It would therefore be desirable to provide an improved telemetry system for transmitting digital data from an implanted pacer so as to avoid the problem of distortion. The telemetry system of the present invention utilizes a pulse generator having an output period proportional to its input voltage magnitude. The telemetered digital data corresponding to conditions of the pacer may be recovered in an external programming/receiver unit by a pulse period detector which generates an analog signal whose magnitude is proportional to each pulse period from the pulse generator.

SUMMARY OF THE INVENTION

Accordingly, it is a general object of the present invention to provide an improved telemetry system for transmitting digital data from an implanted pacer which is implemented with simpler circuits than those traditionally available.

It is an object of the present invention to provide a telemetry system for transmitting digital data from an implanted pacer which utilizes CMOS integrated circuits having low power consumption.

It is another object of the present invention to provide a telemetry system for transmitting digital data from an implanted pacer which includes a pulse generator having an output period proportional to its input voltage magnitude.

It is still another object of the present invention to provide a telemetry system for transmitting internal signals corresponding to pacer conditions from an implanted pacer so as to eliminate the need of surgery for removing and checking of the pacer.

It is yet another object of the present invention to provide a telemetry system for transmitting digital data corresponding to conditions present within the heart so as to eliminate the need for external sensing leads.

In accordance with these aims and objectives, the present invention is concerned with the provision of a telemetry system for transmitting digital data from an implanted cardiac pacer to an external programming/receiver unit which includes an input amplifier responsive to analog internal signals from the implanted pacer for generating amplified analog signals. A variable period pulse generator responsive to the magnitude of the amplified analog signals is provided for generating output pulse signals in which each pulse-to-pulse time interval is variable end is directly proportional to the magnitude of the amplified analog signals. The pulse generator requires only minimum width pulses end there is corresponding minimum system current drain because signal information is contained only in the pulse-to-pulse time interval and not in the pulsewidth. An external programming/receiver unit is provided and includes a pulse period detector which is responsive to the output pulse signals for generatinq reconstructed analog signals corresponding to the amplified analog signals.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 1 is a simplified block diagram of a telemetry system for transmitting digital data from an implanted pacer, constructed in accordance with the principles of the present invention;

FIG. 3 is a more detailed block diagram of the pulse period detector in the external programming/receiver unit of the telemetry system of FIG. 1.

DESCRIPTION OF THE PREFERRRD EMBODIMENT

Figure 2:
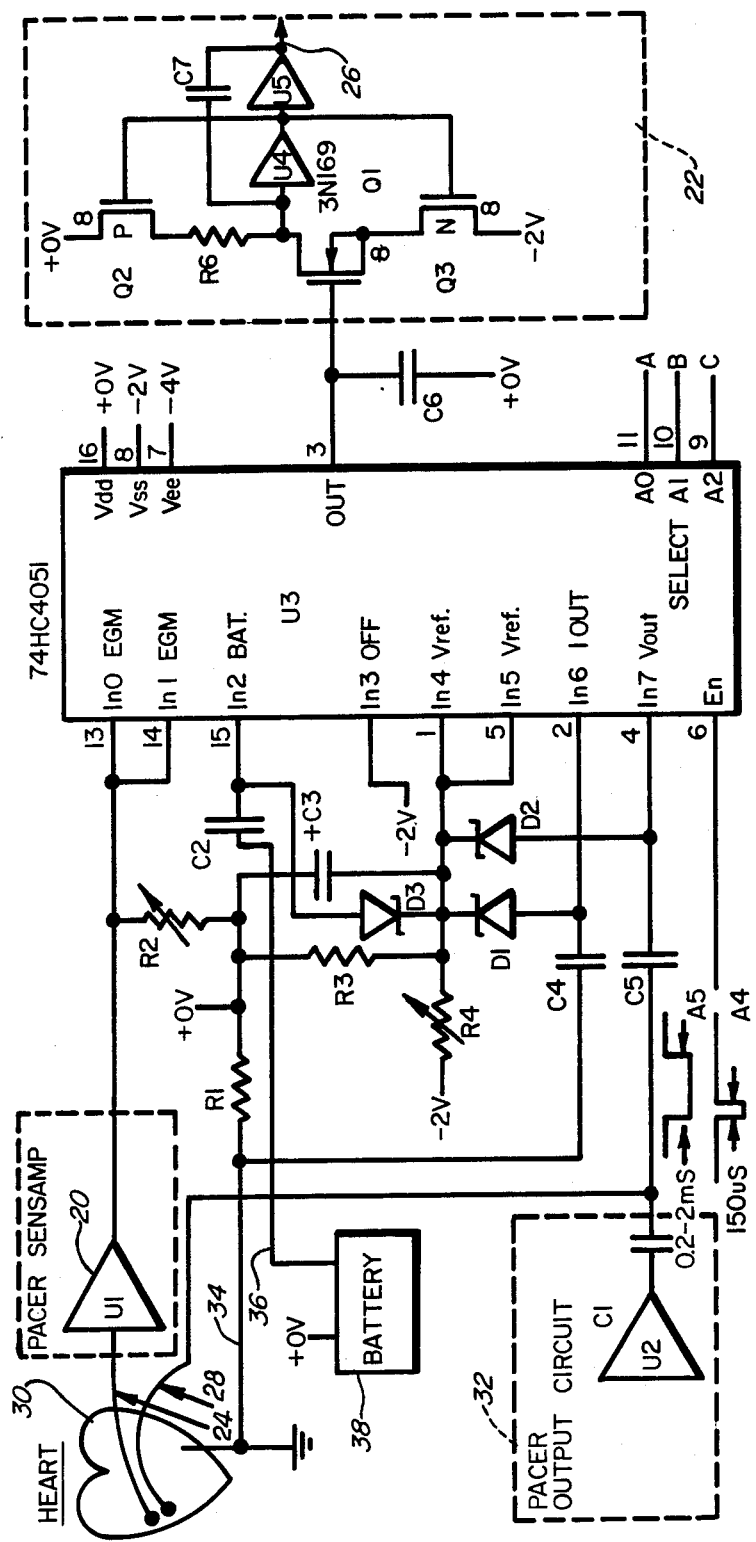
FIG. 2 is a schematic diagram of circuits for use in certain blocks in the implanted pacer of the telemetry system of FIG. 1.

Referring now in detail to the drawings, there is shown in FIG. 1 in a simplified block diagram a telemetry system 10 of the present invention which includes an implanted cardiac pacer 12 and an external programming/receiver unit 14. The implanted pacer 12 transmits digital data via a digital pulse transmission link network 16 to the external receiver unit 14. The link network 16 may consist of an implanted tank circuit in the pacer 12 and a telemetry coil in the external unit 14. The receiver unit 14 includes a pulse period detector 18 which is used to reconstruct the original analog signals from the telemetered digital data that are received.

The implanted pacer 12 includes an amplifier 20 for receiving a small analog intracardiac signal (waveform A1) and for amplifying the same. The amplified analog signal (waveform A2) at the output of the amplifier 20 is applied to the input of a voltage-controlled pulse generator 22 which converts the amplitude of the amplified analog signal A2 to digital pulse signals (waveform F1). Each of the pulse signals in the pulse train from the pulse generator 22 has a pulse-to-pulse time interval or period directly proportional to the magnitude of the amplified analog signal from the amplifier 20. In this manner, there is provided a very simple technique of transmitting internal signals from the implanted pacer 12 in a digital information transmission rather than in an analog information transmission, but which also eliminates the usual steps needed in an analog-to-digital conversion system. In other words, the transmitted information in the present telemetry system is digital and depends on pulse-to-pulse intervals rather than on the level of the analog signals. As a result, the reconstructed signals (waveform A3) from the pulse period detector 18 will be generated more accurately since no distortion will be encountered as in the analog information transmission. The power consumption of this system is minimized since the pulsewidth of the digital pulse signals does not affect the accuracy of the reconstructed signal and the pulsewidths may be of small duration requiring a minimum amount of energy.

Referring now to FIG. 2 of the drawings, there is shown a schematic diagram of circuits for use in certain blocks in the implanted pacer 12 of the telemetry system of FIG. 1. The implanted pacer 12 is provided with an output pacemaker lead 24 which is connected to the input of a sense amplifier U1. The sense amplifier U1 corresponds to the amplifier 20 in FIG. 1 and is used to amplify the intracardiac signals during the electrogram (EGM) mode. The output of the amplifier U1 is connected to one end of a potentiometer R2 and to pins 13 and 14 corresponding to In0 and In1 (EGM mode) of a multiplexer U3. The multiplexer U3 is an integrated circuit type 74HC4051 which is shown with its pin designations and is commercially available from RCA (Radio Corporation of America). The other end of the potentiometer R2 is connected to a ground potential or +0 volts. The potentiometer R2 is used to adjust the center frequency of the pulse generator 22 which is typically set at 4000 Hz during the EGM mode. The EGM analog signal from the amplifier U1 is sent directly via the pins 13 and 14 of the multiplexer U3 to its output on pin 3. The output pin 3 is connected to one end of an output capacitor C6. The other end of the capacitor C6 is connected to the ground potential or +0 volts. The output pin 3 of the multiplexer is also fed to the input of the pulse generator 22. The frequency at the output of the pulse generator 22 on line 26 is directly proportional to the voltage at the output pin 3 of the multiplexer U3.

In addition to the capability of measuring the intracardiac electrical signal directly at the heart via the pacemaker output lead 24, the pacer 12 includes means for measuring additional parameters corresponding to the conditions of the pacer such as voltage output, current output and battery voltage. The measurements are used by a physician to evaluate the operating parameters of the pacer and the battery condition so as to avoid resorting to surgery in order to remove and check the condition of the pacer. The pacer 12 includes a pacemaker input lead 28 for supplying stimulated electrical impulse to the heart 30 of a patient via an output amplifier U2 and a coupling capacitor C1 in the output pacing circuitry 32.

In order to provide an output pulse voltage measurement, the output of the amplifier U2 via the capacitor C1 is connected through an input capacitor C5 to the pin 4 of the multiplexer U3 corresponding to In7. For measuring the output pulse current, a grounded lead 34 of the heart is connected to one and of a resistor R1 and to one and of an input capacitor C4. The other and of the resistor R1 is connected to the ground potential or +0 volts. The other and of the capacitor C4 is connected to the pin 2 of the multiplexer U3 corresponding to In6. For measuring the battery voltage, a lead line 36 is connected from negative battery terminal 38 to one and of an input capacitor C2. The other and of the capacitor C2 is connected to the pin 15 of the multiplexer U3 corresponding to In2.

A reference voltage Vref is applied to pins 1 and 5 corresponding to In4 and In5 of the multiplexer U3. This reference voltage is genarated by a supply voltage Vss of −2 volts at pin 8 of the multiplexer in conjunction with a voltage divider formed of a resistor R3 and a potentiometer R4. The supply voltage Vss is from a voltage regulator formed inside the pacer. A bypass capacitor C3 is connected across the resistor R3 to provide a low impedance path for high frequencies. A first Schottky diode D1 has its cathode connected to the pin In4 and its anode connected to the capacitor C4. A second Schottky diode 02 has its cathode also connected to the pin In4 and its anode connected to the capacitor C5. A third Schottky diode D3 has its cathode also connected to the pin In4 and its anode connected to the capacitor C2.

The multiplexer U3 includes an input enable terminal EN which receives an enable pulse. The enable pulse has typically a pulse width of 150 microseconds (waveform A4) which is initiated at the beginning of the pacer pulse (waveform A5) from the amplifier U2. The pacer pulse has a pulse width between 0.2 and 2 milliseconds. The multiplexer has input pins 9, 10 and 11 for receiving respective addresses A0, A1 and A2 for selacting one of the input signals on the pins In0 and In1, In2, In6, and In7. Upon receipt of the enable pulse, the selected address at pins 9, 10 and 11 corresponding to either input pin In0 and In1, In2, In6, or In7 is allowed to be connected to the output pin 3 of the multiplexer.

During the quiescent state when no measurements are being made, the input capacitors C2, C4 and C5 are charged up to the reference voltage Vref through the respective diodes D3, D1 and D2. Since these are Schottky diodes, there is a low forward voltage drop of approximately 0.2 volts across each diode. When the multiplexer U3 is turned on to perform a measurement, or during a transition, a voltage division will occur between one of the input capacitors C2, C4 or C5 dependent upon the particular measurement selected by the multiplexer and the output capacitor C6. Now the original charge on the selected input capacitor will be changed since some of its charge will be transferred to the output capacitor C6. In order to restore the charge on the input capacitor to its original value, the corresponding diode provides a pull-up function so as to raise the voltage at the input capacitor after the transition or measurament occurs. When the transient from the pulses occur, the respective diodes provide a blocking function so as to not effect a change in the charges.

Prior to the measurement, the pins In4 and In5 are selected by the multiplexer which allows the output capacitor C6 to charge up to the reference voltage Vref. Now when it is desired to obtain a measurement of the battery voltage, the pin In2 is selected by the addresses and a voltage transition is coupled to the output pin 3 via the input capacitor C2. Thus, the transient voltage is divided between the capacitor divider formed by the input capacitor C2 and the output capacitor C6. Then, the pin In2 will be deselected so as to be disconnected from the output pin 3. However, the output voltage will be held by the capacitor C6. The pulse generator 22 will oscillate at a frequency proportional to this output voltage. This oscillation frequency will be telemetered out via the digital pulse transmission link network 16. Alternately, this frequency may be measured by pacer digital counters, stored in the pacer memory and then transmitted through a digital telemetry link.

The voltage-controlled variable period pulse generator 22 includes a field-effect transistor Q1, a resistor R6 and a rate capacitor C7. The transistor Q1 has its drain connected to one end of the resistor R6 and to one end of the capacitor C7. The gate of the transistor Q1 defining the input of the pulse generator 22 is connected to the output pin 3 of the multiplexer U3 at the output capacitor C6. The pulse generator further includes a P-channel MOS transistor Q2, an N-channel MOS transistor Q3, a first buffer U4 and a second buffer U5. The P-channel transistor Q2 has its source connected to the ground potential, its drain connected to the other end of the resistor R6, and its gate connected to the output of the first buffer U4. The input of the first buffer U4 is connected to the drain of the field-effect transistor Q1. The second buffer U5 has its input connected to the output of the first buffer U4 and its output connected to the other end of the rate capacitor C7 and to the output line 26 defining the output of the pulse generator 22.

The N-channel transistor Q3 has its drain connected to the source of the field-effect transistor Q1, its source connected to the supply potential Vss, and its gate connected to the output of the first buffer amplifier U4. The resistor R6 determines the charge up rate of the capacitor C7 and the discharge rate of the capacitor C7 is controlled by the transistor Q1. The output frequency of the pulse generator on the output line 26 is a function of the voltage applied to the gate of the field-effect transistor Q1. It will be appreciated that the pulse generator has been fabricated with CMOS integrated circuits having low power consumption.

As previously pointed out, the output of the pulse generator 22 is sent via the transmission link network 16 to the external programming/receiver unit 14 which includes the pulse period detector 18. In Figure 3, there is shown a more detailed block diagram of the pulse period detector of FIG. 1. The pulse period detector 18 includes an oscillator 42 having a fixed oscillation frequency and a counter 44 connected to the output of the oscillator 42. The output of the counter 44 is fed to the input of a latch 46. The counter 44 and the latch 46 are operatively connected to receive the digital pulse signals F1. The output of the latch 46 is connected to the input of a digital-to-analog converter 48. The counter 44 is used to count the number of pulses from the oscillator 42 appearing in the time interval between any two pulses from the pulse generator 22. Thus, the count will be directly proportional to the time interval between any two pulses. This count is stored in the latch 46 each time a pulse occurs from the pulse generator and is converted to an analog level by the digital-to-analog converter 48.

In this manner, the original analog signal (waveform A1) from the implanted pacer is recovered to produce the reconstructed signal A3 appearing at the output of the digital-to-analog converter 48. It should be understood to those skilled in the art that a microprocessor having a microprogram could also be used to determine the pulse-to-pulse interval of the pulses from the pulse generator 22.

From the foregoing detailed description, it can thus be seen that the present invention provides an improved telemetry system for transmitting digital data from an implanted pacer to an external programming/receiver unit which includes a voltage-controlled pulse generator having an output period proportional to its input voltage magnitude. Further, the telemetry system of the present invention includes a pulse period detector in the receiver unit which generates a reconstructed signal whose amplitude is proportional to each pulse period from the pulse generator.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. A system for transmitting digital data from an implanted cardiac pacer to an external programming/receiver unit comprising:
    input means responsive to analog internal signals from an implanted pacer for generating amplified analog signals; and
    variable period pulse generator means responsive to the magnitude of said amplified analog signals for generating output pulse signals in which the pulse-to-pulse time interval is variable and is directly proportional to the magnitude of said amplified analog signals and the signal information is contained within the pulse-to-pulse interval whereby the width of the pulses may be minimal;
    said pulse generator means comprising an input capacitor, an output capacitor, a field effect transistor having its gate coupled to the output capacitor, means forming a voltage divider network from said capacitors with the output frequency of the pulse generator means being directly proportional to the analog signals across the output capacitor.

2. A system as claimed in claim 1, wherein said input capacitor comprises first, second and third input capacitors selectively coupled to the output capacitor to form a capacitor divider network therewith.

3. A system as claimed in claim 2, further comprising multiplexer means interconnected between said input capacitor and said output capacitor for selectively coupling one of said first, second and third input capacitors to said output capacitor.

4. A system as claimed in claim 3, further comprising a first Schottky diode coupled between said first input capacitor and said multiplexer means.

5. A system as claimed in claim 4, further comprising a second Schottky diode coupled between said second input capacitor and said multiplexer means.

6. A system as claimed in claim 5, further comprising a third Schottky diode coupled between said third input capacitor and said multiplexer means.

7. A system as claimed in claim 1, including an external programming/receiver unit having pulse period detector means responsive to said pulse signals for generating a reconstructed analog signal corresponding to said amplified analog signals, said pulse period detector means comprises oscillator means, counter means, latch means and diqital-to-analog converter means, said counter means being connected between said oscillator means and said latch means, said latch means being connected between said counter means and said converter means, said converter means and said latch means being responsive to and connected to receive said output pulse signals from said pulse generator means via said digital transmission link means for counting the number of pulses from said oscillator means between each pulse-to-pulse time interval of said output pulse signals and for storing a count representative of the time interval between pulses, said converter means being responsive to said latch means for converting said count to an analog level to generate the reconstructed analog signal.

8. In a telemetry system for pacing in which a pacer is implanted in a patient, the improvement comprising in combination:
input means responsive to analog internal signals from an implanted pacer for generating amplified analog signals;
variable period pulse generator means responsive to the magnitude of said amplified analog signals for generating output pulse signals in which pulse-to-pulse time interval is variable and is directly proportional to the magnitude of said amplified analog signals, the signal information being contained within the pulse-to-pulse interval whereby the width of the pulses may be minimal;
said pulse generator means including an output capacitor coupled to receive said amplified analog signals and a field-effect transistor, said field-effect transistor having its gate connected to said output capacitor, the output frequency of said pulse generator means being directly proportional to the voltage across said output capacitor;
said pulse generator means further including a ground potential, a supply potential, a resistor, a rate capacitor, a P-channel MOS transistor, an N-channel MOS transistor, a first buffer, and a second buffer, said P-channel transistor having its source connected to the ground potential and its drain connected to the drain of said field-effect transistor via said resistor, said N-channel transistor having its drain connected to the source of said field-effect transistor and its source connected to the supply potential, said first buffer having its input connected to the drain of said field-effect transistor and its output connected to the gates of said P-channel and N-channel transistors, said second buffer having its input connected to the output of said first buffer and its output connected to the input of said first buffer via said rate capacitor;
an external programming/receiver unit and digital transmission link means for transmitting said output pulse signals to said external programming/receiver unit; and
said external programming/receiver unit including pulse period detector means being responsive to and connected to receive said pulse signal for generating a reconstructed analog signal correspondinig to said amplified analog signals.

9. In a telemetry system as claimed in claim 8, wherein said input means comprises first, second and third input capacitors and multiplexer means for selectively coupling one of said first, second and third input capacitors to the output capacitor to form a capacitor divider network therewith.

10. In a telemetry system as claimed in claim 9, further comprising a first Schottky diode connected between said first input capacitor and said multiplexer means.

11. In a telemetry system as claimed in claim 10, further comprising a second Schottky diode connected between said second input capacitor and said multiplexer means.

12. In a telemetry system as claimed in claim 11, further comprising a third Schottky diode connected between said third input capacitor and said multiplexer means.

* * * * *